US006046310A

United States Patent [19]
Queen et al.

[11] Patent Number: 6,046,310
[45] Date of Patent: Apr. 4, 2000

[54] FAS LIGAND FUSION PROTEINS AND THEIR USES

[75] Inventors: Cary L. Queen; William P. Schneider, both of Los Altos; Maximiliano Vasquez, Palo Alto, all of Calif.

[73] Assignee: Protein Design Labs., Inc., Fremont, Calif.

[21] Appl. No.: 08/815,190

[22] Filed: Mar. 11, 1997

Related U.S. Application Data

[63] Continuation-in-part of application No. 08/614,584, Mar. 13, 1996, abandoned.

[51] Int. Cl.$^7$ .................................................. C07K 16/00
[52] U.S. Cl. ..................................... 530/391.7; 530/391.1
[58] Field of Search .............................. 424/193.1, 194.1, 424/195.11; 530/391.7, 391.1

[56] References Cited

U.S. PATENT DOCUMENTS

| | | |
|---|---|---|
| 4,634,664 | 1/1987 | Oestberg . |
| 5,223,409 | 6/1993 | Ladner et al. . |
| 5,266,491 | 11/1993 | Nagata et al. . |

FOREIGN PATENT DOCUMENTS

| | | |
|---|---|---|
| 0 528 767 | 2/1993 | European Pat. Off. . |
| 0 451 216 | 1/1996 | European Pat. Off. . |
| 5-305975 | 11/1993 | Japan . |
| 5-342526 | 12/1993 | Japan . |
| WO 91/17271 | 11/1991 | WIPO . |
| WO 92/01047 | 1/1992 | WIPO . |
| WO 92/20791 | 11/1992 | WIPO . |
| WO 93/12227 | 12/1992 | WIPO . |
| WO 93/11162 | 6/1993 | WIPO . |
| WO 93/12227 | 6/1993 | WIPO . |

OTHER PUBLICATIONS

Takahashi et al. Cell vol. 76:969–976, 1994.
S. Nagata et al. (1995) *Science* 267:1449. The Fas Death Factor.
R. Watanabe–Fukunaga et al. (1992) *J. Immunol.* 148:1274.
C. Thompson (1995) *Science* 267:1456. Apoptosis in the Pathogenesis and Treatment of Disease.
B. Trauth et al. (1989) *Science* 245:301. Monoclonal Antibody–Mediated Tumor Regression by Induction of Apoptosis.
S. Yonehara et al. (1989) *J. Exp. Med.* 169:1747.
T. Suda et al. (1993) *Cell* 75:1169.
D. Lynch et al. (1994) *Immunity* 1:131.
T. Takahashi et al. (1994) *Cell* 76:969.
T. Takahashi et al. (1994) *Internet. Immunol.* 6:1567.
T. Griffith et al. (1995) *Science* 270:1189. Fas Ligand–Induced Apoptosis as a Mechanism of Immune Privilege.
Rouvier et al. (1993) *J. Exp. Med.* 177:195.
T. Suda and S. Nagata (1994) *J. Exp. Med.* 179:873.
D. Banner et al. (1993) *Cell* 73:431.
D. Kagi (1994) *Science* 265:528. Fas and Perforin Pathways as Major Mechanisms of T Cell–Mediated Cytotoxicity.
S. Nagata and T. Suda (1995) *Immunol. Today* 16:39.
J. Dhein et al. (1995) *Nature* 373:438. Autocrine T–cell suicide mediated by APO–1/(Fas/CD95).
D. Bellgrau (1995) *Nature* 377:630. A role for CD95 ligand in preventing graft rejection.
J. Ogasawara (1993) *Nature* 364:806. Lethal effect of the anti–Fas antibody in mice.
Bird et al. (1988) *Science* 242:423. Single–Chain Antigen–Binding proteins.
*Fundamental Immunology*, W.E. Paul, ed., Raven Press (1993).
*Sequences of Proteins of Immunologic Interest*, 5th ed., E. Kabat et al., U.S. DHHS, (1991).
M. S. Co et al. (1992) *J. Immunol.* 148:1149.
J. Sambrook et al. *Molecular Cloning: A Laboratory Manual* 2nd ed., Cold Spring Harbor Laboratory Press (1989).
E. Harlow et al. *Antibodies: A Laboratory Manual* Cold Spring Harbor Laboratory (1988).
*Methods in Enzymology* vol. 182, Guide to Protein Purification, MP Deutscher, ed., Academic Press, (1990).
L. Aguilar–Bryan et al. (1995) *Science* 268:423. Cloning of the β Cell High–Affinity Sulfonylurea Receptor: A Regulator of Insulin Secretion.
Co. et al. (1996) *Cancer Research* 56:1118.
C. Elson et al. (1995) *Gastroenterology* 109:1344.

*Primary Examiner*—Christina Y. Chan
*Assistant Examiner*—Patrick J. Nolan
*Attorney, Agent, or Firm*—Townsend & Townsend & Crew LLP

[57] ABSTRACT

Fas ligand fusion proteins comprising a polypeptide capable of specifically binding an antigen or a cell surface marker are prepared employing recombinant DNA technology for use in, e.g., treatment of autoimmune disorders.

8 Claims, 7 Drawing Sheets

```
  1 CAG CCC CGA GAA CCA CAG GTG TAC ACC CTG CCC CCA TCC
  1 Gln Pro Arg Glu Pro Gln Val Tyr Thr Leu Pro Pro Ser

40 CGG GAG GAG ATG ACC AAG AAC CAG GTC AGC CTG ACC TGC
 14 Arg Glu Glu Met Thr Lys Asn Gln Val Ser Leu Thr Cys

79 CTG GTC AAA GGC TTC TAC CCC AGC GAC ATC GCC GTG GAG
 27 Leu Val Lys Gly Phe Tyr Pro Ser Asp Ile Ala Val Glu

118 TGG GAG AGC AAT GGG CAG CCG GAG AAC AAC TAC AAG ACC
 40 Trp Glu Ser Asn Gly Gln Pro Glu Asn Asn Tyr Lys Thr

157 ACA CCT CCC ATG CTG GAC TCC GAC GGC TCC TTC TTC CTC
 53 Thr Pro Pro Met Leu Asp Ser Asp Gly Ser Phe Phe Leu

196 TAC AGC AAG CTC ACC GTG GAC AAG AGC AGG TGG CAG CAG
 66 Tyr Ser Lys Leu Thr Val Asp Lys Ser Arg Trp Gln Gln

235 GGG AAC GTC TTC TCA TGC TCC GTG ATG CAT GAG GCT CTG
 79 Gly Asn Val Phe Ser Cys Ser Val Met His Glu Ala Leu

274 CAC AAC CAC TAC ACG CAG AAG AGC CTC TCC CTG TCT CCG
 92 His Asn His Tyr Thr Gln Lys Ser Leu Ser Leu Ser Pro

313 AGT AAA GGT ACC CAG CTC TTC CAC CTA CAG AAG GAG CTG
105 Ser Lys Gly Thr Gln Leu Phe His Leu Gln Lys Glu Leu

352 GCA GAA CTC CGA GAG TCT ACC AGC CAG ATG CAC ACA GCA
118 Ala Glu Leu Arg Glu Ser Thr Ser Gln Met His Thr Ala

391 TCA TCT TTG GAG AAG CAA ATA GGA TCC CCC AGT CCA CCC
131 Ser Ser Leu Glu Lys Gln Ile Gly Ser Pro Ser Pro Pro

430 CCT GAA AAA AAG GAG CTG AGG AAA GTG GCC CAT TTA ACA
144 Pro Glu Lys Lys Glu Leu Arg Lys Val Ala His Leu Thr

469 GGC AAG TCC AAC TCA AGG TCC ATG CCT CTG GAA TGG GAA
157 Gly Lys Ser Asn Ser Arg Ser Met Pro Leu Glu Trp Glu

508 GAC ACC TAT GGA ATT GTC CTG CTT TCT GGA GTG AAG TAT
170 Asp Thr Tyr Gly Ile Val Leu Leu Ser Gly Val Lys Tyr
```

FIG. 6.

```
547 AAG AAG GGT GGC CTT GTG ATC AAT GAA ACT GGG CTG TAC
183 Lys Lys Gly Gly Leu Val Ile Asn Glu Thr Gly Leu Tyr

586 TTT GTA TAT TCC AAA GTA TAC TTC CGG GGT CAA TCT TGC
196 Phe Val Tyr Ser Lys Val Tyr Phe Arg Gly Gln Ser Cys

625 AAC AAC CTG CCC CTG AGC CAC AAG GTC TAC ATG AGG AAC
209 Asn Asn Leu Pro Leu Ser His Lys Val Tyr Met Arg Asn

664 TCT AAG TAT CCC CAG GAT CTG GTG ATG ATG GAG GGG AAG
222 Ser Lys Tyr Pro Gln Asp Leu Val Met Met Glu Gly Lys

703 ATG ATG AGC TAC TGC ACT ACT GGG CAG ATG TGG GCC CGC
235 Met Met Ser Tyr Cys Thr Thr Gly Gln Met Trp Ala Arg

742 AGC AGC TAC CTG GGG GCA GTG TTC AAT CTT ACC AGT GCT
248 Ser Ser Tyr Leu Gly Ala Val Phe Asn Leu Thr Ser Ala

781 GAT CAT TTA TAT GTC AAC GTA TCT GAG CTC TCT CTG GTC
261 Asp His Leu Tyr Val Asn Val Ser Glu Leu Ser Leu Val

820 AAT TTT GAG GAA TCT CAG ACG TTT TTC GGC TTA TAT AAG
274 Asn Phe Glu Glu Ser Gln Thr Phe Phe Gly Leu Tyr Lys

859 CTC TAA
287 Leu ***
```

FAS LIGAND FUSION PROTEINS AND THEIR USES

CROSS-REFERENCE TO RELATED APPLICATION

This application is a continuation-in-part of 08/614,584 filed Mar. 13, 1996, now abandoned, the contents of which are incorporated by reference.

FIELD OF THE INVENTION

The present invention relates generally to the combination of recombinant DNA and monoclonal antibody technologies to develop novel compounds for the suppression of T-cell mediated immune responses, including responses directed against the patient's own tissues in autoimmune and inflammatory conditions or against transplanted tissues.

BACKGROUND OF THE INVENTION

The Fas protein is a type I membrane protein that belongs to the tumor necrosis factor (TNF) receptor family (see S. Nagata et al., *Science*, 267:1449, 1995). Many tissues and cell lines weakly express Fas, but abundant expression is found in the heart, lung, liver, ovary and thymus (R. Watanabe-Fukunaga et al., *J. Immunol.* 148:1274, 1992). In addition, Fas is highly expressed on activated lymphocytes including T cells (Nagata et al., op. cit.). Fas transmits a signal for apoptosis or programmed cell death (see C. Thompson, *Science* 267:1456, 1995) when it is triggered by binding of certain antibodies such as APO-1 (B. Trauth et al., *Science* 245:301, 1989) and anti-Fas (S. Yonehara et al., *J. Exp. Med.* 169:1747, 1989). Apoptotic cell death is characterized by nuclear and cytoplasmic shrinkage, membrane blebbing, and degradation of chromosomal DNA in a characteristic pattern, and can be distinguished from necrotic cell death due to acute cellular injury (Thomson, op. cit.).

The natural ligand for Fas is known simply as the Fas ligand (FasL). Its rat (T. Suda et al., *Cell* 75:1169, 1993), mouse (D. Lynch et al., *Immunity* 1:131, 1994; T. Takahashi et al., *Cell* 76:969, 1994) and human (T. Takahashi et al., *Internat. Immunol.* 6:1567, 1994) forms have been cloned at the cDNA level. FasL is a type II membrane protein, i.e, having an extracellular carboxyl terminal domain and an intracellular amino terminal domain, and belongs to the TNF family of proteins (T. Suda et al., op. cit.). The Fas ligand is strongly expressed on activated lymphocytes, in the testis (T. Suda et al., op. cit.) and the eye (T. Griffith et al., *Science* 270:1189, 1995), as well as on some cytotoxic T-lymphocyte (CTL) cell lines (Rouvier et al., *J. Exp. Med.* 177:195, 1993).

Transfectant cells expressing FasL, as well as purified FasL protein (T. Suda and S. Nagata, *J. Exp. Med.* 179:873, 1994), are cytotoxic for cells expressing Fas. Thus, FasL transmits a signal for apoptosis by binding to Fas. More precisely, by analogy with the homologous TNF—TNF receptor system, whose molecular structure has been determined by X-ray crystallography (D. Banner et al., *Cell* 73:431, 1993), FasL is believed to function as a trimer. Also by analogy with TNF, the FasL trimer presumably binds one to three Fas molecules at the interface of respective FasL units (as schematically illustrated in FIG. 1). Binding of two or more Fas molecules to a FasL trimer presumably causes dimerization of Fas, which transmits an apoptotic signal to the Fas-expressing cell.

Fas-FasL induced cytotoxicity is one of the two major mechanisms of CTL-mediated cytotoxicity (D. Kagi, *Science* 265:528, 1994). The Fas system is believed to play an important role in the clonal deletion of peripheral autoreactive T cells and in control of the immune response (S. Nagata and T. Suda, *Immunol. Today* 16:39, 1995; J. Dhein et al., *Nature* 373:438, 1995), as mice with inactivating mutations in Fas (lpr mice) or FasL (gid mice) develop generalized lymphoproliferation and autoimmunity.

In addition, it has recently been discovered that mouse testis tissue transplanted into allogeneic mice is not rejected, presumably because the FasL expressed on the Sertoli cells of the testis destroys activated Fas-expressing T cells that would otherwise attack the transplanted tissue (D. Bellgrau, *Nature* 377:630, 1995). Similarly, expression of FasL in the eye is sufficient to destroy infiltrating inflammatory cells and make the eye an "immune privileged" site with reduced susceptibility to immune response and inflammation (T. Griffith et al., *Science* 270:1189, 1995). Also, cotransplantation of allogeneic pancreatic islet cells with myoblasts expressing FasL in mice protected the islet cells from immune rejection (H. Lau et al., *Science* 273:109, 1996).

This ability of FasL to destroy activated T cells suggests that it has potential as an immunosuppressive drug. However, FasL is likely to be highly toxic when injected into animals and humans, because it will induce apoptosis of other cells expressing Fas in addition to T cells, for example liver cells. Indeed, an agonistic antibody to murine Fas rapidly kills mice after intraperitoneal administration by causing massive necrosis of the liver, presumably mediated through apoptosis of hepatocytes via Fas (J. Ogasawara, *Nature* 364:806, 1993). Thus, compounds incorporating FasL that have specific cytotoxicity to autoimmune T cells and low non-specific toxicity are required for treatment of autoimmune disease and transplant rejection. The present invention fulfills these and other needs.

SUMMARY OF THE INVENTION

The present invention provides novel fusion proteins that comprise a functional moiety of the extracellular domain of the FasL protein and a polypeptide capable of specifically binding to a cell surface marker such as an antigen. The fusion protein may also comprise a linker, e.g., of from 8 to 40 amino acids in length, which may be from a human protein. The binding polypeptide can be an antibody, preferably a human or humanized antibody, and often of the IgG2 or IgG4 isotype. The fusion protein will preferably have reduced ability to cause the death of cells expressing the Fas protein, relative to Fas ligand protein, but increased ability to cause the death of such cells when in the presence of the cells to which the binding polypeptide binds. In one embodiment, the FasL component will contain an amino acid substitution that reduces its tendency to form dimer, trimer, or other aggregates. DNA segments encoding the fusion proteins and cell lines producing them may be prepared by a variety of recombinant DNA techniques.

The fusion proteins may be utilized or the treatment of various autoimmune or other inflammatory conditions, including multiple sclerosis, rheumatoid arthritis, type I diabetes, inflammatory bowel disease, psoriasis, rejection of an organ transplant, or ischemia-reperfusion injury, as well as for treatment of cancer. For such use, the fusion proteins will be substantially pure and formulated in a pharmaceutically acceptable dosage form. For treatment of a particular autoimmune disease, the binding polypeptide component of the fusion protein will bind preferentially to cells of the tissue under attack that disease, for example to neurons, pancreatic beta cells, synovial cells, or colonic thelial cells.

BRIEF DESCRIPTION OF THE FIGURES

FIG. 6. Nucleotide (SEQ ID NO:15) and amino acid (SEQ ID NO:16) sequence of the CH3/FasL domain of an Ig-FasL fusion protein. Amino acid positions 1 to 106 comprise $C_H3$. Residues 107 and 108 result from the addition of a KpnI site. Residues 109 to 287 constitute the extracellular domain of FasL with a His to Ser substitution at position 139.

DETAILED DESCRIPTION OF THE INVENTION

In one aspect, the present invention is directed to a fusion protein comprising a functional moiety of the extracellular domain of the FasL protein and a polypeptide capable of specifically binding to a cell surface marker, such as an antigen, expressed on particular cell-type(s) or tissue(s). In a preferred embodiment, the binding polypeptide comprises the variable domain of an antibody. In a particularly preferred embodiment, the antibody is humanized, human or from another primate species. However, the binding polypeptide may also comprise, for example, the binding site of a cellular receptor; a receptor ligand such as a cytokine, lymphokine, interleukin, growth factor, hormone or the like; or the binding site of an adhesion molecule, such as a selectin or integrin. A large number of such binding proteins are known to those skilled in the art (see, e.g., Fundamental Immunology, 3rd ed., W. E. Paul, ed., Raven Press, 1993, which is hereby incorporated by reference). As used herein, the term "cell surface marker" refers to a carbohydrate, glycolipid, etc. but most often a protein which localizes to the plasma membrane of a cell and a portion of which is exposed to the extracellular region (e.g., an integral membrane protein or a transmembrane glycoprotein), wherein said extracellular portion can be specifically bound by an antibody or other ligand, i.e., with an affinity of stronger than about $1 \times 10^6 M^{-1}$. The term cell surface marker also refers to a polynucleotide sequence encoding such a cell surface protein. Various cell surface proteins can be used as cell surface markers, including, for example, a CD (cluster of differentiation) antigen present on cells of a hematopoietic lineage (e.g., CD2, CD4, CD8, CD21, etc.), γ-glutamyltranspeptidase, an adhesion protein (e.g., ICAM-1, ICAM-2, ELAM-1, VCAM-1), hormone, growth factor and cytokine receptors, ion channels, and the membrane-bound form of an immunoglobulin μ chain. Preferably, a cell surface marker protein is a protein which is normally expressed at significant levels on the cells to be treated, and may be selected for use in the methods and constructs of the invention on the basis of the practitioner's desired application. By definition, the recognition or functional moiety of the extracellular domain of the FasL protein preferably contains at least the determinants required to bind to the Fas protein and transmit an apoptotic signal under treatment conditions. Typically, FasL fragments comprised in the recognition domain will contain only a portion of the extracellular domain. Such fragments will preferably retain the binding specificity of an intact FasL polypeptide, but will be soluble rather than membrane bound. Preferably, the FasL component of the fusion protein is found within a segment of up to about 10, 25 or 50 amino acids within the FasL extracellular region.

Figure 1:
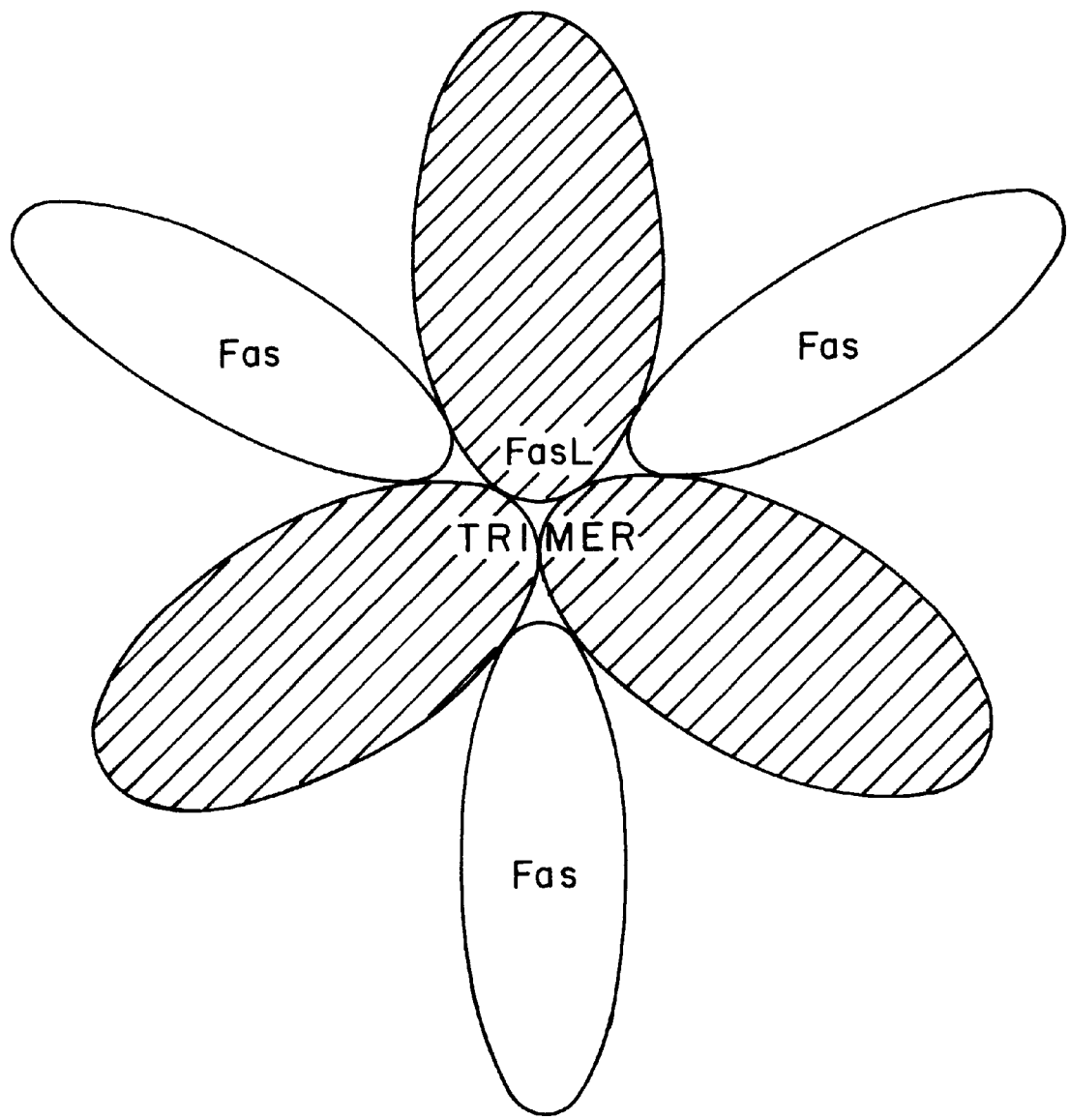
FIG. 1. Schematic diagram of the presumed structure of the Fas—Fas ligand complex. Fas ligand (FasL) is presumed to form a trimer.
Figure 2:
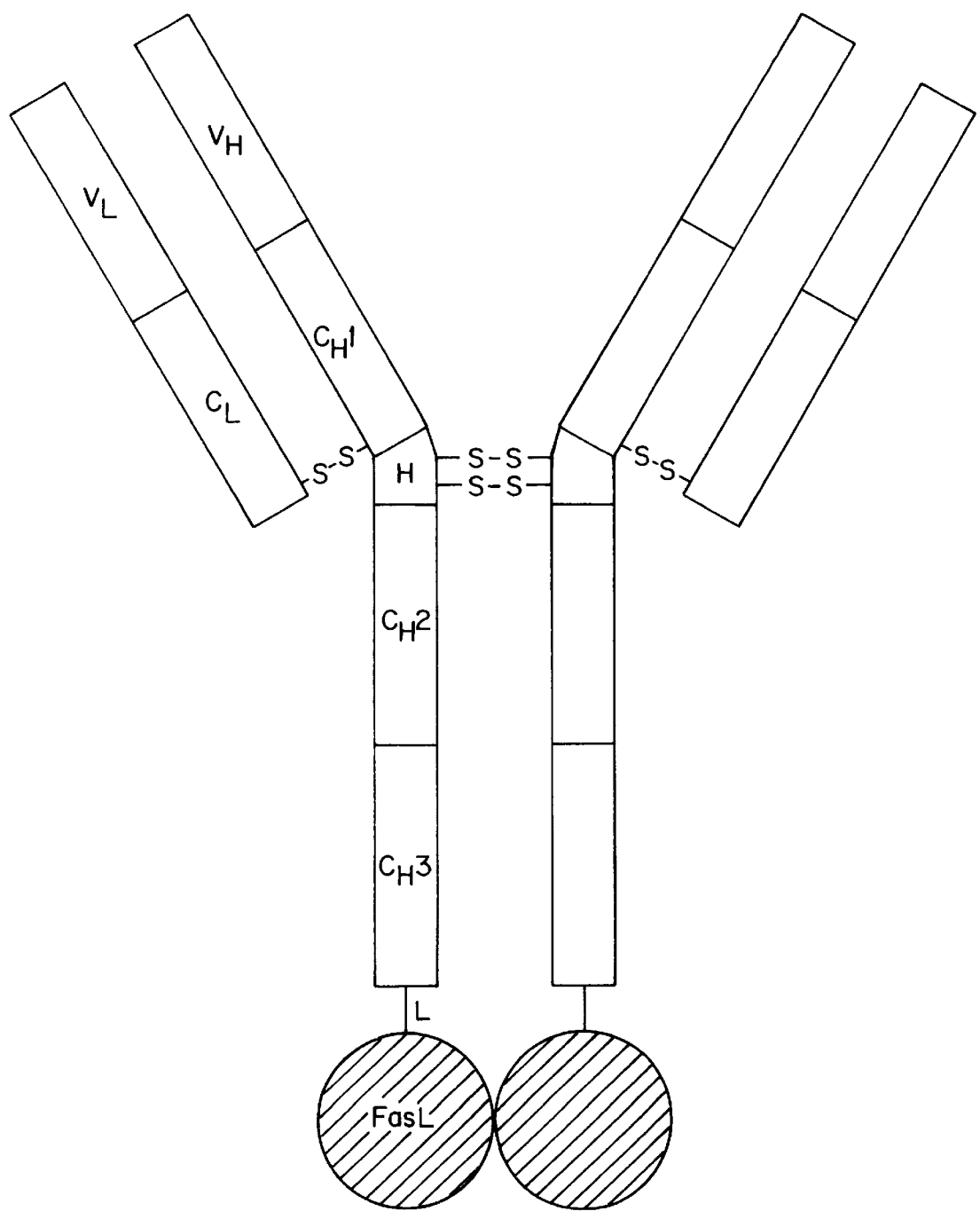
FIG. 2. Schematic diagram of an Ig-FasL fusion protein, with the domains of the antibody labeled. S—S, disulfide bond; L, linker.

An example of a preferred embodiment of the invention is diagrammed in FIG. 2. Such an embodiment, in which the FasL domain is linked to an immunoglobulin (Ig), is denoted Ig-FasL. The illustrated immunoglobulin (antibody) may bind to any epitope on the surface of particular cells or tissues. The optional polypeptide linker (L) between the C-terminal domain of the antibody and the FasL moiety is preferably made so as to allow the two FasL moieties in the dimeric molecule to themselves dimerize, and may contain from 1 to about 100 amino acids, preferably 8 to 50 amino acids and most preferably 12–35 amino acids. Examples of preferred linkers are the 34 extracellular amino acids of FasL that are proximal to the membrane, possibly with one or more amino acid substitutions, or a part of this sequence, or the sequence $(Gly_4Ser)_N$ (SEQ ID NO:17) where N is from 1 to 8, preferably 3 to 6. In preferred embodiments, the sequence of the linker will be essentially (i.e., at least about 75% but preferably 80%, 90%, 95% or more) identical to a sequence occurring in a natural human protein in order to reduce immunogenicity of the fusion protein. The linker will generally have a sufficient number of hydrophilic residues to be adequately soluble in water, and may contain a significant number of glycines and/or prolines in order to give it the degree of flexibility or rigidity desired.

Such linkers may also be used to connect other types of binding polypeptides and the FasL moiety. The linker may be attached to the binding polypeptide or FasL moiety, or those domains attached directly, via non-peptide or non-covalent bonds, for example via a disulfide bond, a chemical cross-linker, or leucine zipper peptides such as jun/fos (see, e.g., PCT/US92/10140 [WO 93/11162], which is incorporated herein by reference). Art-known chemical cross-linkers that can be suitable for this purpose include homobifunctional linkers such as N-hydroxysuccinimide esters, e.g., dithiobis(succinimidyl propionate) (DSP), and heterobifunctional linkers such as N-succinimidyl-3-(2-pridyldithio)-propionate (SPDP) and other cross-linkers listed in the Pierce Chemical Company catalog or well-known in the art, which may be used according to the manufacturer's suggestions and recommendations or the art. The FasL domain will preferably be attached to the carboxy terminus of the binding polypeptide, but may also be attached to the amino terminus or elsewhere. Each monomer of Ig-FasL has two polypeptide chains—an antibody light chain and a heavy chain/FasL fusion chain—but other FasL fusion proteins may have fewer or more chains.

In other preferred embodiments, one or more domains of the antibody molecule are deleted, for example the $C_H3$ and/or $C_H2$ domains, or these domain(s) and the hinge and/or $C_H1$ domains. Alternatively, the antibody may be a single-chain antibody (see, e.g., Bird et al., Science 242:423, 1988, which is incorporated herein by reference) or have only one domain or be bispecific (e.g., PCT/US92/10140, which is incorporated herein by reference). The resulting fusion protein may be dimeric or monomeric. In preferred embodiments, the antibody constant region is human, and the antibody is of the IgG class, especially IgG2 or IgG4 to reduce effector function, but possibly IgG1 or IgG3. However, constant regions from other mammalian, especially rodent or primate, species may be used, as well as the IgD, IgM, IgA or IgE isotypes. Various amino acid substitutions, deletions and/or insertions may also be made in the antibody component. For example, one or more amino acids in positions 234 to 237 of $C_H2$ may be substituted (using the numbering scheme of the human Eu antibody and counting from the amino terminus of the heavy chain), e.g., with alanine, to reduce or eliminate binding to the Fc receptors (see commonly assigned US 08/656,586, wherein amino acids 234 and 237 of IgG2 are substituted with alanine). Substitutions in the antibody or FasL moiety may also be made to eliminate glycosylation sites, introduce or eliminate disulfide bonds, improve solubility or stability, or provide other desirable properties. The positions of some glycosylation sites in FasL are given in Suda et al., op. cit. or may be determined from the sequence. Instead of using the natural Fas ligand protein in FasL fusion proteins, other "Fas ligand" proteins (polypeptides) that bind to Fas and transmit an apoptotic signal may be used, for example polypeptides comprising the variable domains of anti-Fas antibodies such as APO-1, or novel polypeptides that bind to Fas found using phage display methods (see U.S. Pat. No. 5,223,409, which is incorporated by reference).

In a preferred embodiment, the fusion protein will have reduced ability to cause the apoptosis of cells expressing the Fas protein (target cells), e.g., activated T cells, transfectant cells expressing Fas, or hepatocytes. That is, at least 2–3 times as much, preferably at least 10 or 100 times as much, and most preferably 1000 or more times as much fusion protein as soluble FasL protein or extracellular domain alone will be required to induce a given amount of apoptosis or cell death (e.g., 50%, 75%, 90% or essentially 100%) in the target cells. On the other hand, in preferred embodiments, the fusion protein will have greater effectiveness in causing the apoptosis or death of target cells, especially activated T cells or cytotoxic T lymphocytes (CTLs) or Fas-expressing transfectants or cancer cells, in the presence of other cells to which the binding polypeptide of the fusion protein specifically binds (the binding cells). That is, in the presence of a sufficient number of binding cells (typically from about 0.1 to 1 or 10 times as many as target cells), at least 2–3 times less, preferably at least 10 or 100 times less, and most preferably 1000 or more times less, fusion protein will be required to induce a given amount of cell death in the target cells, relative to FasL protein, or relative to fusion protein in the absence of binding cells. A fusion protein that has reduced ability to apoptose target cells relative to FasL, and increased effectiveness in the presence of binding cells, is said to be "specifically cytotoxic" for the target cells.

Figure 3:
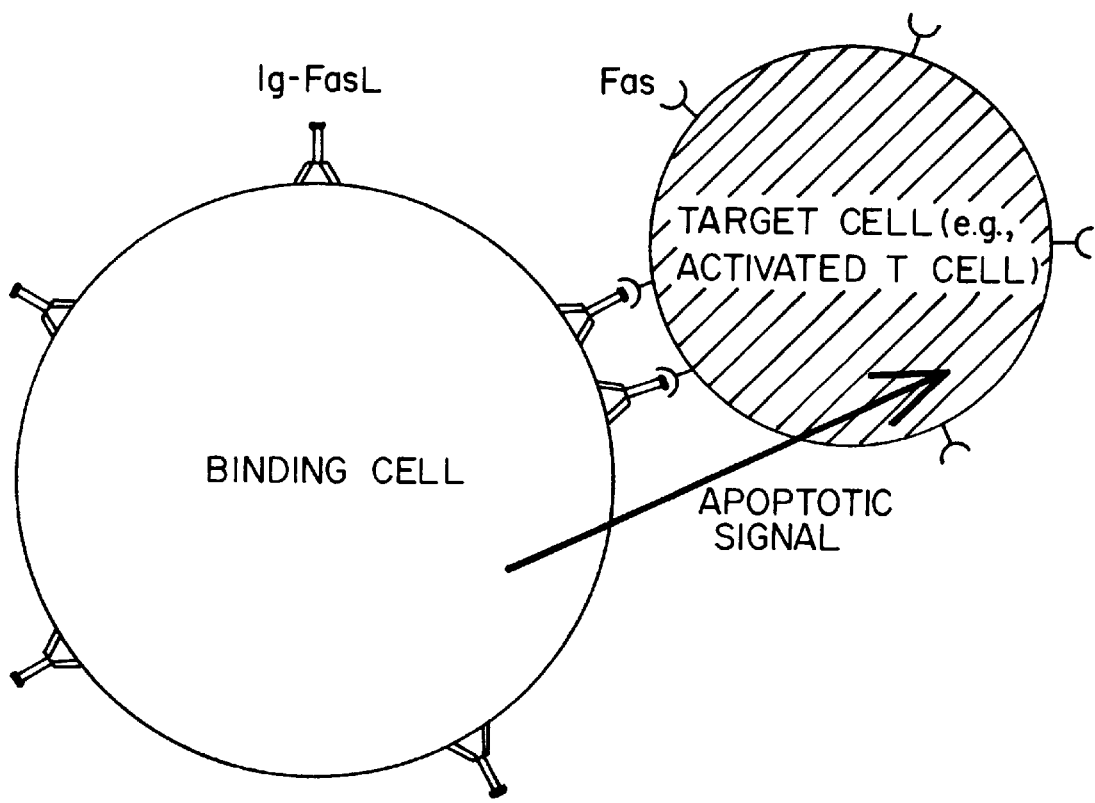
FIG. 3. Schematic diagram of the mechanism by which an Ig-FasL or other FasL fusion protein apoptoses Fas-expressing cells in the presence of cells to which the Protein binds ("binding cells").

Without being bound by theory, the inventors believe that the fusion protein has reduced ability to apoptose target cells alone because within the fusion protein, the FasL moiety forms monomers or dimers and not trimers. This property can be further enhanced by mutation of critical amino acids involved in the trimerization of FasL, determined by in vitro mutagenesis experiments or by analogy to the known structure of the TNF trimer. Such a monomer or dimer is expected to bind only a single Fas molecule, which is not sufficient to cause the dimerization or aggregation of Fas needed to transmit an apoptotic signal to the target cell. However, once the fusion protein has bound to the surface of the binding cell, the simultaneous binding of multiple fusion protein molecules on the surface of that cell to Fas molecules on the target cell can aggregate those Fas molecules and induce an apoptotic signal with increased effectiveness, as illustrated in FIG. 3. Similarly, the fusion protein has the ability to kill cells that express both the target of the binding polypeptide and Fas.

Thus, in one aspect the fusion protein of the present invention has a reduced ability, in vivo or in vitro, relative to soluble FasL protein or its extracellular domain, to cause death of cells expressing Fas protein. Moreover, the novel fusion proteins will also have an increased ability, in vivo or in vitro, to cause death of a first population of cells expressing Fas protein, when such first population of cells are in the presence of a second population of cells to which the polypeptide binds, relative to the absence of such second population of cells.

As alluded to above, in a preferred embodiment of the invention, the FasL moiety of the FasL fusion protein comprises amino acid substitutions or mutations that further reduce its ability to form dimers, trimers or higher oligomers or aggregates, especially when in solution. This further enhances the desirable properties described above, e.g., decreases the ability of the fusion protein to kill cells expressing Fas, especially relative to soluble FasL protein or extracellular domain. However, the fusion protein with amino acid substitutions still has the ability to cause death of a first population of cells (e.g., cells within the first population) expressing Fas protein when such first population of cells are in the presence of a second population of cells to which the polypeptide binds, further increased relative to the absence of such second population of cells.

Preferred amino acid substitutions for this purpose disrupt the subunit-subunit interface of FasL so as to disfavor formation of the trimer in solution, but without disabling the potential reconstitution of an aggregate state once the fusion protein has bound to a cell surface via its binding polypeptide component. Such substitutions should preferably not affect the amino acids involved in binding of FasL to Fas. One approach to determining such substitutions is to align FasL with the homologous protein TNF-α. The alignment is, in turn, used to map structure-activity data collected in the TNF system to the FasL system, and also forms the basis for the construction of a 3-dimensional structure model of FasL and of the FasL-Fas complex based on the known crystal structure of the TNF—TNF receptor complex (D. Banner et al., *Cell* 73:431, 1993, which is incorporated herein by reference), using homology methods well-known to those skilled in the art of molecular model building.

Based on this analysis, substitutions were made in the FasL polypeptide extracellular domain. Substitutions are described using the 1-letter amino acid code and with the numbering referring to the position of the residue in the FasL sequence of Takahashi et al., *Internat. Immunol.* 6:1567, 1994 (which is incorporated herein by reference, and which is provided in Table 4). In the FasL sequence provided in Table 4, the extracellular domain extends from about residue 103 to the carboxy terminus. It will be appreciated that the FasL sequence of Table 4 is provided by way of illustration (e.g., to identify specific amino acid residues that may be advantageously mutated) and not by way of limitation. As used herein, when the fusion protein of the invention is derived from naturally occuring FasL protein, the FasL protein may be a human FasL protein (including variants, e.g., allelic variants), a non-human FasL protein, or a FasL polypeptide containing deletions or insertions (e.g., from about 5 to about 20 amino acids or more), or substitutions (e.g., conservative substitutions) compared to a naturally occuring FasL sequence.

The substitutions H148S (i.e., substitution of histidine by serine at position 148), Y189A, Y192A, and Y244A, were derived from the analogous mutations shown to affect TNF-α structure (X.-M. Zhang et al., *J. Biol. Chem.*, 267:24069, 1992, which is incorporated herein by reference; these four substitutions also satisfy the geometric criteria specified below). An additional set of substitutions came from analysis of the subunit-subunit interface in the structural model of FasL derived as described above. These mutations, I168A, L170A, M229A, Y232A, and V248A, correspond to positions distant from the Fas-FasL contact region, but involved in inter-subunit interaction. Other substitutions may be derived from the geometric criteria that the amino acids are at least about 7 Å away from Fas in the model of the Fas-FasL complex, and that at least one of their atoms is within extended van der Waals contact with any atom in a different FasL subunit. ("Extended" van der Waals contact means that the standard van der Waals radii have been increased by the radius of a water molecule; i.e., by 1.4 Å). This additional set includes amino acids T234, R241, S242, L245, G246, A247, F249, S272, Y279, and L281. All these amino acids may be substituted with any of the other 20 standard amino acids, especially with alanine. Other substitutions reducing the ability of FasL to form dimers, trimers, etc. may be found by respectively mutagenizing each amino acid of FasL, for example by replacement with alanine, followed by expression and characterization of the product. Combinations of 2, 3 or more of the substitutions in FasL may be constructed to achieve additive effects.

In another aspect, the invention is directed to recombinant DNA segments that encode all or part of the FasL fusion protein. In the case of an Ig-FasL fusion protein, an exemplary DNA sequence encoding the $C_H3$-linker-FasL portion of the molecule is shown in FIG. 6. Sequences of the antibody light chain as well as the $V_H$, $C_H1$, hinge, $C_H2$ and $C_H3$ domains are well-known (see Sequences of Proteins of Immunologic Interest, 5th ed., E. Kabat et al., U.S. Department of Health and Human Services, 1991, which is incorporated herein by reference), and are readily available or may be cloned or synthesized in cDNA, genomic, or synthetic form using a variety of methods well-known in the art from, e.g., B cells or hybridomas. The V regions of particular antibodies of interest may be readily cloned using, e.g., anchored PCR (see M. S. Co et al., *J. Immunol.* 148:1149, 1992). Sequences encoding other polypeptide binding proteins have been or may similarly be cloned using art-known methods. Sequences encoding FasL are also known (T. Suda et al., op. cit. and T. Takahashi et al., op. cit.) and may be obtained or re-cloned using, e.g., polymerase chain reaction (PCR). For use in human patients, the human Fas ligand sequence will preferably be used, but the FasL from other species may also be used, especially for testing.

The DNA segments will typically further include expression control sequences operably linked to the fusion protein coding sequences, including a promoter, ribosome binding site, and polyadenylation and/or transcription termination sites. The fusion protein may be expressed by transfecting the DNA segments, generally contained on plasmid vectors, into bacterial, yeast, plant, insect or preferably mammalian cells, using calcium-phosphate, electroporation or other art-known methods. For expression in eucaryotic cells, the promoter and optional enhancer are preferably derived from, e.g., inmmunoglobulin genes, SV40, retroviruses, cytomegalovirus, elongation factor 1α (U.S. Pat. No. 5,266,491, which is incorporated by reference) and the like. Preferred host cell lines include CHO cells, COS cells, HeLa cells, NIH 3T3 cells, and various myeloma or hybridoma cell lines including Sp2/0 and NS/0. The plasmid vector will also generally contain a selectable marker such as gpt, neo, hyg or dhfr, and an amp, tet, kan, etc. gene for expression in *E. coli*. A variety of plasmid vectors suitable for expression of heterologous proteins including FasL fusion proteins in a variety of cell types are well-known and readily available in the art. The DNA segments will typically encode a leader sequence at the amino terminus of the fusion protein chain (s) to enable secretion of the fusion protein, e.g., for Ig-FasL the leader sequences naturally associated with the antibody are suitable.

Construction of the DNA segments encoding the fusion protein, their linkage to expression control sequences and insertion into plasmids, and transfection into cells and selection and optional gene amplification of fusion protein-expressing cell lines may all be performed by a variety of methods well-known in the arts of genetic engineering and cell culture including restriction enzyme digests, ligation, oligonucleotide synthesis and PCR (see, e.g., J. Sambrook et al., Molecular Cloning: A Laboratory Manual, 2nd ed., Cold Spring Harbor Laboratory Press, 1989, which is hereby incorporated by reference). Mouse or other antibodies to serve as binding polypeptides have been or may be derived using a variety of methods well-known in the art of immunology and hybridoma technology, including i.p. or footpad immunization in adjuvant and fusion of immune B cells with immortalized myeloma cells (see, e.g., E. Harlow et al., Antibodies: A Laboratory Manual, Cold Spring Harbor Laboratory, 1988, which is hereby incorporated by reference). Such antibodies can be humanized using published methods including CDR-grafting and framework substitution (see European Patent 0451216 and application 92903551.7, and U.S. Pat. No. 5,585,089, each of which is incorporated by reference). Alternatively, human antibodies can be derived directly using trioma methodology (see U.S. Pat. No. 4,634,664 which is incorporated by reference), transgenic animals (e.g, WO 93/12227 and U.S. Pat. No. 5,569,825 each of which is incorporated by reference), or phage display methods (see WO 91/17271 and WO 92/01047), including chain shuffling (WO 92/20791). Each of the aforementioned references is incorporated herein by reference.

Once a transfectant cell line has been selected that expresses and secretes the FasL fusion protein, it may optionally be adapted to grow in serum-free media (e.g., Hybridoma SFM from Gibco BRL) by passaging in decreasing concentrations of serum, and may be subcloned. The fusion protein may then be purified from (preferably serum-free) media in which the expressing cell line has been grown by standard procedures of the art including filtration, precipitation, protein A affinity chromatography, gel filtration, ion exchange chromatography, electrophoretic methods and the like (see, e.g., Methods in Enzymology, vol. 182, Guide to Protein Purification, M. P. Deutscher, ed., Academic Press, 1990, which is hereby incorporated by reference). Substantially pure preparations of the fusion protein, i.e., at least 90 to 95% homogeneity and preferably 98 to 99% or higher, are preferred for pharmaceutical uses.

For administration to patients, the FasL fusion protein will typically be formulated in a pharmaceutically acceptable carrier. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make the solution isotonic. The carrier may also contain excipients such as human serum albumin, polysorbate 80, sugars or amino acids to protect the active protein. The concentration of fusion protein in these formulations may vary widely from about 0.01 to 100 mg/ml but will most often be in the range 1 to 10 mg/ml. The formulated FasL fusion protein is particularly suitable for parenteral administration, and may be administered as an intravenous infusion or by subcutaneous, intramuscular or intravenous injection, and may also be administered by injection at the site of disease, e.g., intracranially or into the joints.

In another aspect, the invention is directed to the use of the FasL fusion proteins of the present invention as drugs for treatment of autoimmune disease. The fusion proteins are used to treat a wide variety of autoimmune diseases, such as those listed in Fundamental Immunology, op. cit., but especially those which are organ or tissue-specific and/or which are mediated by T cells. Diseases which are especially suitable for treatment with FasL fusion proteins include rheumatoid arthritis, multiple sclerosis, inflammatory bowel disease (ulcerative colitis and Crohn's disease) and insulin-dependent diabetes (type I diabetes). Other suitable diseases include myasthenia gravis, pemphigus vulgaris, idiopathic thrombocytopenic purpura (ITP), and autoimmune vasculitis. Systemic lupus erythematosus and other non-organ specific autoimmune diseases are also possible. The FasL fusion protein also finds use in the treatment of other types of inflammation, such as due to ischemia and reperfusion (e.g., after myocardial infarction, stroke or hemorrhagic shock), or in inflamatory disorders of the skin, such as psoriasis.

The FasL fusion proteins will also find use as drugs for treatment of cancers, such as leukemias, lymphomas, sarcomas and carcinomas including tumors of the breast, colon, lung, prostate, pancreas and other organs. For such use, the binding polypeptide will bind to a cell surface marker expressed on the cancer cells, usually to a greater extent than on normal cells. Many such tumor-associated cell surface markers are well known in the art. The cancer cells will also express Fas, so that when the FasL fusion protein binds to a cancer cell, the FasL moiety can kill that or neighboring cancer cells by delivering an apoptotic signal through their Fas. For example, the binding polypeptide may be a humanized ABL 364 antibody which binds to the Lewis y antigen expressed on many tumors including those mentioned above, and the FasL fusion protein may then be used to treat patients with those tumors including those mentioned above. Exemplary humanized ABL 364 antibodies are described in EP 92810633.5, in Co et al., *Cancer Res*. 56:1118, 1996, and U.S Pat. No. 5,562,903 (each of which is incorporated by reference in its entirety and for all purposes). A humanized ABL 364 antibody also referred to as hu-BR55-2 comprises light and heavy chain variable regions that are described in, e.g., FIG. 3 of Co et al., 1996, supra; FIGS. 12 and 13 of U.S Pat. No. 5,562,903; and in Table 5 infra.

Doses of the drug will typically contain from about 0.01 to about 100 mg FasL fusion protein, but most often from about 0.1 to about 10 mg. The dose chosen will be an amount sufficient to alleviate the disease without causing unacceptable side effects as determined, e.g., in a phase II clinical trial. It may be administered once or multiple times, e.g., 1 to 3 times per day, week or month for one to several days, weeks, months or years, or chronically, depending upon the nature and severity of the disease. The FasL fusion proteins will often be administered in combination with other drugs, for example, corticosteroids, non-steroidal anti-inflammatory drugs, cyclosporin A, or methotrexate, or with thrombolytics (e.g., tPA) in the case of ischemia, according to medical practice and the judgement of the physician. The FasL fusion proteins are particularly suitable for co-administration with humanized antibodies, for example against the IL-2 receptor (see European Patent 0451216) or adhesion molecules (see EP 94903357.5 and WO 94/12215, both of which are incorporated by reference).

To treat a particular autoimmune disease, the binding polypeptide portion of the FasL fusion protein is chosen to preferentially or specifically bind to the cells or tissue under attack in that disease. After treatment, the FasL moiety of the fusion protein will then protrude from the surface of the binding cells and preferably destroy any inflammatory cells, for example cytolytic T cells, that would otherwise infiltrate and damage the affected tissue (see FIG. 3). For example, to treat multiple sclerosis, the binding polypeptide would typically bind to the surface of neurons or Schwann cells. Thus, the binding polypeptide may for example be an antibody that binds to myelin basic protein or other components of the myelin sheath, or to a receptor for a neurotransmitter, or may comprise the binding domain of a neurotrophic factor. To treat rheumatoid arthritis, the binding polypeptide should bind to proteins expressed specifically in the joints, for example on cells of the synovium. To treat type I diabetes, the binding polypeptide can bind to a protein expressed on the membrane of pancreatic beta cells, e.g., to GLUT-2 or to the sulphonylurea receptor (see L. Aguilar-Bryan et al., *Science* 268:423, 1995). To treat inflammatory bowel disease, the FasL fusion protein may bind epithelial cells of the colon by comprising an antibody binding to, e.g., sialyl Lewis a or E-cadherin. For myasthenia gravis, the binding polypeptide is preferably an antibody to the acetylcholine receptor; and for ITP, it is an antibody specifically binding to platelets, e.g., to the gpIIb/IIIa glycoprotein.

Thus, for each cell type under attack in an autoimmune disease, a variety of cell surface markers suitable as targets for binding polypeptides are well known in the art of biology. Preferably, the binding polypeptide of the FasL fusion protein should not substantially down-modulate its target upon binding, which would reduce the number of sites available for the FasL fusion protein to bind and therefore the density of FasL on the cell surface. Also, preferably, the binding polypeptide should not substantially inhibit or stimulate the function of its target, which would interfere with the normal function of the binding cells. However, because of the variety of epitopes on a target protein, it is generally easy, e.g., to generate an antibody that does not inhibit the function of the target, as is well-known in the art. In some cases, it will be sufficient for the FasL fusion protein to bind to neighboring cells of those actually under attack, e.g., to other pancreatic cells instead of or in addition to beta cells in treating diabetes. Alternatively, the FasL fusion protein may bind to non-cellular components of the tissues under attack, for example to protein components of basement membranes, or to collagen in the case of rheumatoid arthritis.

To assay the FasL fusion protein in vitro, increasing concentrations of the fusion protein (e.g. from 0.001 ng/ml to 1000 ng/ml) are incubated with Fas expressing cells, e.g. W4 transfectant cells or T cells or neutrophils, and lysis of the Fas expressing cells measured, e.g., by a $^{51}Cr$ release assay. See, generally, T. Suda et al., op. cit. and T. Suda and S. Nagata, op. cit., which are incorporated herein by reference. As described above, the FasL fusion protein will have reduced ability to cause apoptosis of the cells relative to the FasL protein or extracellular domain alone. In a second experiment, the binding cells for the FasL fusion protein are added to the incubation mix. As described above, the fusion protein will have greater effectiveness in causing the death of the target cells in the presence of the binding cells. For example, as a test case, the binding polypeptide of the fusion protein is the humanized ABL 364 antibody against the Lewis y antigen and the binding cells are SKBR5 or T47D breast carcinoma cells. In additional experiments, other Fas expressing cells are used, for example T cells activated, e.g., by growth in Con A and IL-2, followed by stimulation with PMA and ionomycin.

As an optional second set of in vitro assays, Fas-expressing cells are incubated with binding cells for which they have lytic activity. For example, the binding cells may be K562 or YAC cells or other cells susceptible to lysis by NK cells, and the Fas-expressing cells may be NK cells activated by, e.g., IL-2 and IL-12. Alternatively, the Fas-expressing cells may be T cells activated as above, or cytotoxic T lymphocyte (CTL) cell lines with specificity for the binding cells, which may be, e.g., tumor cell lines or transfected cells. Methods to generate such specific CTL lines are well-known in the art of immunology. The ability of the Fas-expressing cells to lyse the binding cells is assayed by art-known techniques, such as $^{51}$Cr labeling of the binding cells. This ability is measured in the absence and presence of various concentrations of a FasL fusion protein which comprises a binding polypeptide that binds to the binding cells. Presence of the FasL fusion protein inhibits the ability of the Fas-expressing cells to lyse the binding cells, because the FasL fusion protein causes the apoptosis of the "attacking" Fas-expressing cells after it binds to the binding cells, thus protecting them (FIG. 3). This in vitro experiment therefore models the use of FasL fusion proteins to treat autoimmune disease, in which the FasL fusion proteins protect the cells under autoimmune attack by binding to them and apoptosing infiltrating inflammatory cells, as described above.

The FasL fusion proteins can also be assayed in a variety of in vivo animal models. For example, to establish their ability to successfully treat multiple sclerosis, they may be assayed in mouse or rat experimental allergic encephalomyelitis (EAE). To establish their ability to treat rheumatoid arthritis, they may be assayed in collagen- or adjuvant-induced arthritis in rats. Reduction of disease severity in these models is measured by scales that respectively indicate degree of paralysis or joint swelling, as commonly used in the art. Survival after a defined time may also be an appropriate endpoint in certain animal models. Ability to treat diabetes can be modeled in the non-obese diabetic (NOD) mouse or BB rat. A large number of animal models are available to test the treatment of these and other autoimmune diseases (see, e.g., European Patent 0304291 and references cited therein) or other inflammatory diseases (see EP 94903357.5 and references cited therein) including inflammatory bowel disease (see C. Elson et al., *Gastroenterology* 109:1344, 1995). Of course, it is understood that the binding polypeptide of the FasL fusion protein will bind to the appropriate cell type in the animal species used. The ability of FasL fusion proteins to treat cancer is shown by their ability to prevent, inhibit or reverse growth of murine or human tumors in normal or immunocompromised mice.

In the case of each animal model, before, at or after induction of the disease (e.g., 1, 3, 5, 7, 9 or 10–14 or more days after), at least one dose of the appropriate FasL fusion protein is administered, typically i.p. but possibly i.v. or by another route. Multiple doses of the FasL fusion protein may be administered on these or other days. The size of the dose will be scaled from the typical doses described above for human patients, but may be somewhat larger proportionally, i.e., will vary from approximately 1 ng to 1 mg per animal, but most often will be from 1 to 100 µg. The severity of the disease will then be measured on various days after treatment, and compared with untreated or placebo-treated animals. Treatment with the FasL fusion protein will reduce the appropriately measured severity of the disease and may decrease animal mortality.

The FasL fusion proteins will also find other uses. For example, they may be used to prevent or treat rejection of organ transplants, including xenotransplants, by choosing as the binding polypeptide component an antibody that binds specifically to the transplanted organ, e.g., to MHC determinants expressed on it. They may be used in vitro to detect or to lyse Fas-expressing cells in a mixed population of Fas- and non-Fas-expressing cells. They may serve as the detecting reagent in a diagnostic assay, e.g., ELISA assay, for soluble Fas or Fas-expressing cells in patients with leukemia or other disorders.

EXPERIMENTAL

EXAMPLE 1

Cloning of FasL cDNA

A cDNA clone of the human FasL gene is obtained, or cloned again by first synthesizing single strand cDNA from RNA extracted from human FasL expressing cells such an human peripheral blood lymphocytes or activated T lymphocytes, using oligo dT as a primer. Then the cDNA is used as a template for PCR with primers (1) and (2) of Table 1 below, or other primers based on the sequence of the human FasL gene (T. Tabahashi et al., *Internat. Immunol.* 6:1567, 1994, which is incorporated herein by reference).

TABLE 1

Primers used in construction of Ig-FasL fusion protein

| Number | Sequence | |
|--------|----------|---|
| 1 | ATGCATGCTCTAGAATGCAGCAGCCCTTCAATTACCC | (SEQ ID NO:3) |
| 2 | ATGCATGCTCTAGATTAGAGCTTATATAAGCCG | (SEQ ID NO:4) |
| 3 | ACCACAGGTGTACACCCTGC | (SEQ ID NO:5) |
| 4 | ATGCATGCGGTACCTTTACTCGGAGACAGGGAGAGG | (SEQ ID NO:6) |
| 5 | ATGCATGCGGTACCTGAGTGCCACGGCCGGCAAG | (SEQ ID NO:7) |

TABLE 1-continued

Primers used in construction of Ig-FasL fusion protein

| Number | Sequence | |
|---|---|---|
| 6 | GGGAAGTATGTACACGGGG | (SEQ ID NO:8) |
| 7 | AGCAAATAGGATCCCCCAGTCC | (SEQ ID NO:9) |
| 8 | ATGCATGCGGTACCTTAGAGCTTATATAAGCCG | (SEQ ID NO:10) |
| 9 | ATGCATGCGGTACCCAGCTCTTCCACCTACAGAAG | (SEQ ID NO:11) |
| 10 | GGACTGGGGGATCCTATTTGCTTCTCCAAAG | (SEQ ID NO:12) |

EXAMPLE 2

Construction of Ig-FasL in Expression Vector

In this example, an Ig-FasL fusion protein is made that incorporates an antibody of the human IgG2 isotype, utilizing the pVg2 expression vector (FIG. 4), which is the same as pVg1 (Co et al., op cit), except that the XbaI-BamHI segment containing the γ1 constant region has been replaced using standard methods with a genomic segment containing the γ2 constant region. First, a Kpn I site (GGTACC) is introduced between the last coding codon and the termination codon of the IgG2 $C_H3$ domain in pVg2 by PCR as follows. Using the IgG2 $C_H$ gene as template, PCR with primers (3) and (4) of Table 1 above generates a 321 bp fragment that extends from a BsrGI site at the fourth codon through the end of the $C_H3$ coding region. PCR with primers (5) and (6) generates a 101 bp fragment that contains the sequence from the end of the $C_H3$ coding region through the BsrGI site about 80 bp downstream. Both of the PCR product fragments are digested with KpnI and BsrGI, joined at the Kpn I ends, and used to replace the corresponding BsrGI fragment in pVg2.

Figure 5:
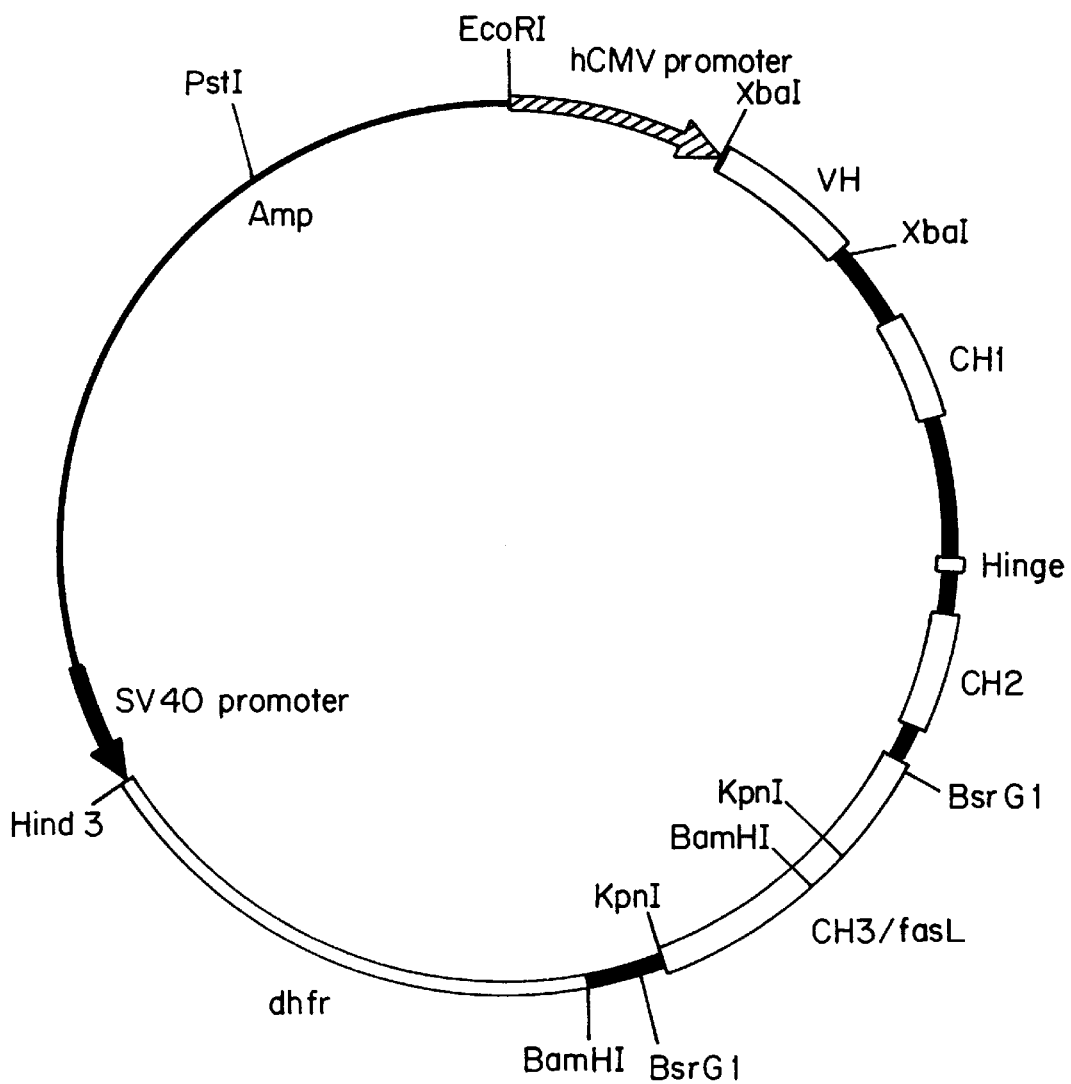
FIG. 5. Schematic diagram of the pVg2FasL expression vector used to express the heavy chain of the Ig-FasL fusion protein, with an antibody heavy chain variable region ($V_H$) inserted at the XbaI site. Key regulatory elements, coding regions, and restriction sites are indicated.

A fusion of the human IgG2 $C_H$ gene and part of the human FasL gene is then constructed in the following manner. A 453 bp BamHI-KpnI DNA fragment encoding the C-terminal extracellular 145 amino acids of human FasL is generated by PCR using the human FasL cDNA clone as template and primers (7) and (8) followed by digestion with KpnI and BamHI. A 93 bp KpnI-BamHI DNA fragment encoding a polypeptide linker is generated by PCR also using the human FasL cDNA clone as template but with primers (9) and (10), again followed by digestion with Kpn I and Bam HI. These two fragments are joined at the Bam HI ends and inserted into the KpnI site at the end of the CH3 coding region of the modified pVg2 plasmid. The resulting encoded fusion protein, which is contained on the pVg2FasL plasnid (FIG. 5), consists of a complete human IgG2 $C_H$ region sequence, followed by Gly and Thr amino acids due to the introduction of the Kpn I site, a polypeptide linker consisting of the membrane domain-proximal 34 amino acids of the extracellular domain of human FasL (amino acids 103 through 136) with a His to Ser substitution at the 31st position, and the 145 C-terminal (extracellular) residues of human FasL. Of course, any desired polypeptide linker, e.g., amino acids 132 through 136 of FasL, can be used instead of the one chosen here by encoding it on a KpnI-BamHI fragment by oligonucleotide synthesis, and using that fragment instead of the 93 bp KpnI-Bam HI DNA fragment described above. Similarly, an analogous construction starting from pVg1 or pVg4 (see EP 94903357.5) or analogously constructed pVg3 vector can be used to generate FasL fusion proteins using antibodies respectively of the IgG1, IgG4 and IgG3 isotypes.

EXAMPLE 3

Expression of Ig-FasL Protein

To express an Ig-FasL protein binding to a particular epitope, the variable regions of an antibody with that specificity are cloned, and the $V_H$ gene including signal sequence and splice donor sequence inserted at the XbaI site of pVg2FasL. The $V_L$ gene of the antibody is similarly cloned into the XbaI site of the light chain expression vector pVk (Co et al., 1992, op cit), and the two expression plasmids co-transfected into an appropriate cell line, such as Sp2/0 cells, by electroporation. Cells are selected for gpt expression and screened for production of IgG2-FasL fusion protein by ELISA using an anti-human light chain capture reagent and an anti-human heavy chain or anti-human FasL detection reagent. The IgG2-FasL fusion protein is purified from culture supernatant of a high-yielding transfectant cell line by protein A affinity chromatography or other chromatographic techniques. As one example, the light and heavy chain genes of the humanized ABL 364 antibody are inserted into the vectors as indicated to express a fusion protein of humanized ABL 364 and FasL.

EXAMPLE 4

Additional Ig-FasL Fusion Protein Constructs

Figure 4:
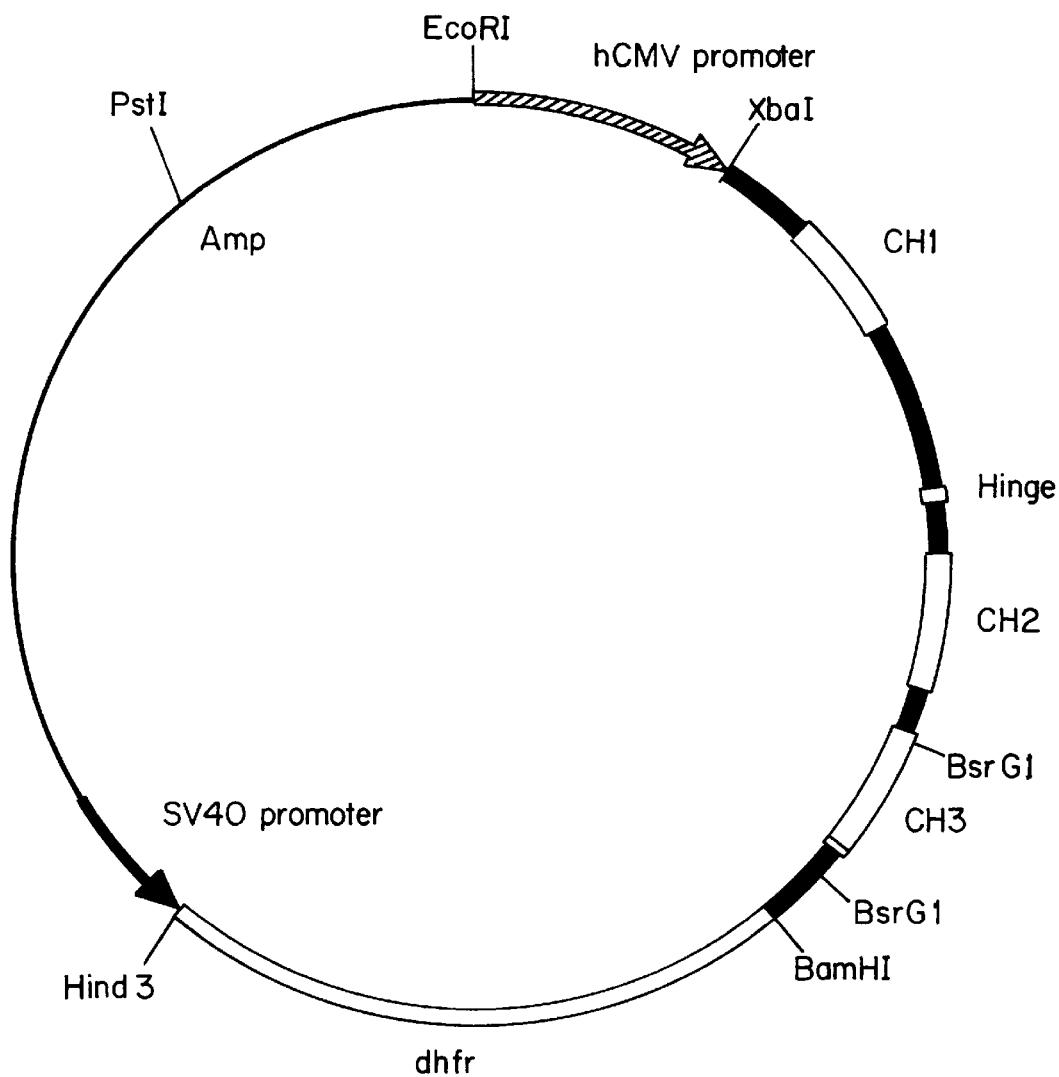
FIG. 4. Schematic diagram of the pVg2 expression vector, with key regulatory elements, coding regions, and restriction sites indicated.

Other expression plasmids encoding Ig-FasL fusion proteins were constructed. As in Example 2, a KpnI site was first introduced between the last coding codon and the termination codon of the human IgG2 heavy chain constant region gene segment in vector pVg2 (FIG. 4 ). Specifically, using pVg2 as template, PCR with the appropriate primers generated a BsrGI-KpnI fragment product extending from the BsrGI site at the fourth codon of the CH3 domain to the end of the CH3 coding region. A second PCR using the same template and other appropriate primers generated a KpnI-BsrGI fragment product extending from the end of the CH3 coding region to the BsrGI site approximately 80 bp downstream. These two PCR products were joined at the KpnI site ends and used to replace the corresponding BsrGI fragment of pVg2. The resulting plasmid was designated pVg2Kpn.

Also similarly to Example 2, KpnI fragments encoding the extracellular portion of human FasL preceded by a short FasL linker region of either 5 or 34 amino acid residues were generated by PCR with the appropriate primers and using the human FasL cDNA clone as template. Each of these fragments was inserted into the KpnI site of pVg2Kpn to generate plasmids encoding fusion polypeptides consisting of a human IgG2 heavy chain constant region followed by a Gly Thr dipeptide due to the introduction of the KpnI site, a 5 or 34 residue FasL linker, and the extracellular human FasL domain. These plasmids were designated pVg2hFasL5 and pVg2hFasL34.

Complete heavy chain-FasL genes were constructed by inserting an XbaI fragment encoding the heavy chain variable region of the humanized ABL 364 antibody denoted HuABL364 (M. S. Co et al., Cancer Res. 56: 1118, 1996, incorporated herein by reference) into the XbaI site upstream of the heavy chain constant region coding region in plasmids pVg2hFasL5 and pVg2hFasL34. The resulting plasmids were designated pABLhFasL5 and pABLhFasL34 respectively.

To provide a selectable marker on the pABLhFasL5 and pABLhFasL34 plasmids, the 1.5 kb HindIII-BamHIII fragment containing the dhfr gene was replaced with the 2.3 kb Hind III-Bam HI fragment from pSV2neo (P. J. Southern and P. Berg, *J. Mol. Appl. Genet.*, 1:327, 1982) that encodes the gene for neomycin resistance. The resulting plasmids were designated pABLhFasL5neo and ABLhFasL34neo.

EXAMPLE 5

Expression of HuABL364 Ig-FasL Fusion Proteins

Humanized ABL 364 Ig-FasL fusion proteins were expressed in both stably and transiently transfected cells. NIH 3T3 cells were stably co-transfected with the plasmids pABLhFasL5neo or pABLhFasL34neo together with the HuABL364 light chain expression plasmid phABLTEWL (M. S. Co et al., Cancer Res. 56: 1118, 1996) using the liposome reagent Lipofectamine (GibcoBRL) following the manufacturer's protocol. Transfected cells were selected for resistance to the drug G418.

COS7 cells were transiently co-transfected with phABLTEWL and either pABLhFasL5 or pABLhFasL5neo, or pABLhFasL34 or pABLhFasL34neo, using Lipofectamine (GibcoBRL) following the manufacturer's protocol. Ig-FasL protein produced by the former plasmids contains the 5 amino acid linker between the Ig and FasL and is denoted HuABL364 Ig-FasL5, whereas Ig-FasL protein produced by the latter plasmids contains the 34 amino acid linker and is denoted HuABL364 Ig-FasL34; the two forms are generically denoted HuABL364 Ig-FasL.

Production of HuABL364 Ig-FasL protein by stable and transient transfectants was demonstrated by ELISA and immunoprecipitation. ELISA analysis utilized either of two capture reagents, a polyclonal goat anti-human gamma chain reagent (Biosource, #AHI1301) and a mouse monoclonal anti-human FasL antibody (Pharmingen, #65321A). The developing reagent was a peroxidase-conjugated goat anti-human kappa chain antibody (Biosource, #AHI0804 or Southern Biotech, #2060-05). In an ELISA with either capture reagent, the stably transfected cells gave a positive signal above background, showing that the secreted protein contained both the human gamma chain and FasL components.

HuABL364 Ig-FasL protein was imrmunoprecipitated from culture supernatents of transiently transfected cells using either protein A Sepharose 4B (Sigma) or goat anti-human IgG agarose (Sigma) following art-known procedures. Polyacrylamide gel electrophoresis (PAGE) under denaturing and reducing conditions of the immunoprecipitated protein yielded bands of the expected size for HuABL364 Ig-FasL upon staining with Coomasie Blue. HuABL364 Ig-FasL was purified from culture supernatents of transiently or stably transfected cells by affinity chromatography on protein G columns.

EXAMPLE 6

Characterization of HuABL364 Ig-FasL

The ability of HuABL364 Ig-FasL to bind Fas on the cell surface via the FasL domain was demonstrated by flow cytometry. MOLT-4, a human T lymphocyte line that expresses Fas on the cell surface (B. Trauth et al., *Science*, 245:301, 1989, incorporated herein by reference) but not the antigen for HuABL364, was stained by incubation with protein G-purified HuABL364 lg-FasL followed by incubation with an anti-human IgG FITC reagent (Jackson Immunoresearch, #715-096-151). Positive staining by HuABL364 Ig-FasL was detected by flow cytometry, compared to negative staining with the HuABL364 antibody. Moreover, an anti-Fas mouse monoclonal antibody (Calbiochem, fas Ab-2) inhibited staining by HuABL364 Ig-FasL, demonstrating that binding of HuABL364 Ig-FasL to MOLT-4 cells was due to FasL-Fas interaction, and therefore that FasL was functional in the Ig-FasL construct.

The ability of protein G-purified HuABL364 Ig-FasL to kill cells by apoptosis was determined by flow cytometry using a commercially available assay based on cell staining by annexin V and propidium iodine, following the manufacturers protocol (R&D Systems, Minneapolis, Minn.; cat. # KNX50). HuABL364 Ig-FasL, both soluble and bound to a solid phase (i.e., plastic surface), demonstrated apoptotic activity toward CESS cells (Table 2), a human B lymphocyte that expresses Fas (B. Trauth et al., *Science*, 245:301, 1989, incorporated herein by reference).

TABLE 2

Apoptotic activity toward CESS cells of HuABL364 Ig-FasL

| Protein | Phase | % apoptotic cells |
|---|---|---|
| HuABL364 Ig-FasL34 | solution | 61.0% |
| HuABL364 Ig-FasL34 | solid phase | 44.6% |
| Anti-Fas IgG antibody | solution | 15.3% |
| Anti-Fas IgG antibody | solid phase | 41.3% |
| No protein | | 11.8% |

To determine whether the apoptotic activity of the soluble HuABL364 Ig-FasL is due to oligomerization of the protein, a sample was analyzed using an HPLC gel filtration column (Tosohaas G3000 SW). A substantial amount of the Ig-FasL eluted at a position corresponding to a molecular weight of about 600,000 Daltons, suggesting that aggregates of the protein are formed. This is likely to be a result of interaction between FasL domains of multiple Ig-FasL molecules.

EXAMPLE 7

Construction and Analysis of IR-FasL Mutant Fusion Proteins

KpnI fragments encoding the nine FasL mutants H148S, Y189A, Y192A, Y244A, I168A, L170A, M229A, Y232A, and V248A described above were generated by PCR using the appropriate primers and pABLhFasL5neo as template. The KpnI fragment for each mutant was inserted into pABLhFasL5neo, replacing the wild type fragment, resulting in expression plasmids encoding the heavy chain—FasL mutant polypeptides.

The mutant and wild type HuABL364 Ig-FasL were expressed by transient transfection of COS7 cells as described above. The presence of Ig-FasL protein in the culture supernatents of transiently transfected cells was verified by ELISA using the anti-human gamma and anti-FasL capture reagents as described above. The culture supernatants of the transfected cells containing the respective HuABL364 Ig-FasL proteins were used for further experiments, with supernatant from untransfected cells serving as a negative control.

The apoptosis-inducing activity of the wild type and mutant Ig-FasL proteins (culture supernatant from transfected cells) was tested, as described above, on two target cell lines: the CESS line described above which expresses Fas but not the ABL 364 antigen, and T47D, a human breast carcinoma cell that expresses both Fas and the ABL 364 antigen. The apoptotic activity of the Ig-FasL proteins fall into three classes (Table 3). One class induces apoptosis in both of the cell lines (wild type, I168A, L170A, M229A, and V248A). A second class is unable to induce apoptosis in either cell line (H148S, Y189A, Y192A, and Y244A). And a third class has activity against T47D cells but not CESS cells (Y232A). The third class is the most preferred in that the Ig-FasL fusion protein has little or no apoptotic activity when in solution, but when cross-linked or aggregated by binding to cells expressing the ABL 364 antigen, demonstrates apoptotic activity. Moreover, such fusion proteins have reduced ability in vitro, relative to soluble FasL protein or FasL protein extracellular domain, to cause death of cells expressing Fas protein.

Ig-FasL fusion proteins (e.g., comprising the humanized ABL 364 variable domain) that have an amino acid substitution at Y232, especially of alanine, will therefore have the ability to cause death in a first population of cells expressing Fas protein when such first population of cells are in the presence of a second population of cells to which the polypeptide binds (e.g., cancer cells that express the Lewis y antigen), increased relative to the absence of such second population of cells.

TABLE 3

Apoptotic activity of HABL364 Ig-FasL mutant fusion proteins

| Mutation in | % apoptotic cells | |
|---|---|---|
| HuABL364 Ig-FasL5 | CESS | T47D |
| No mutation (wild-type) | 88% | 91% |
| H148S | 26% | 15% |
| I168A | 81% | 91% |
| L170A | 87% | 98% |
| Y189A | 24% | 11% |
| Y192A | 25% | 10% |
| M229A | 90% | 95% |
| Y232A | 32% | 88% |
| Y244A | 24% | 16% |
| V248A | 87% | 95% |
| Untransfected supernatant | 27% | 14% |

From the foregoing, it will be appreciated that the FasL fusion proteins of the present invention offer numerous advantages over other treatments for autoimmune disease or cancer. Individual FasL fusion proteins are applicable to many different autoimmune or other inflammatory conditions or cancers, are efficacious, and because they target only the organs and cells involved in a particular disease, have few side effects. They may be readily and economically produced, require only relatively small doses, and generally have little or no immunogenicity.

All publications and patent filings are herein incorporated by reference to the same extent as if each individual publication or patent filing was specifically and individually indicated to be incorporated by reference. Although the present invention has been described in some detail by way of illustration and example for purposes of clarity and understanding, it will be apparent that certain changes and modifications may be practiced within the scope of the appended claims.

TABLE 4

Amino Acid Sequence (SEQ ID NO:2) of FasL,
and FasL Nucleotide Sequence (SEQ ID NO:1)

| 1 | ATG | CAG | CAG | CCC | TTC | AAT | TAC | CCA | TAT | CCC | CAG | ATC | TAC | TGG | GTG | GAC | AGC | AGT | GCC | AGC |
|---|---|---|---|---|---|---|---|---|---|---|---|---|---|---|---|---|---|---|---|---|
| 1 ▸ | Met | Gln | Gln | Pro | Phe | Asn | Tyr | Pro | Tyr | Pro | Gln | Ile | Tyr | Trp | Val | Asp | Ser | Ser | Ala | Ser |
| 61 | TCT | CCC | TGG | GCC | CCT | CCA | GGC | ACA | GTT | CTT | CCC | TGT | CCA | ACC | TCT | GTG | CCC | AGA | AGG | CCT |
| 21 ▸ | Ser | Pro | Trp | Ala | Pro | Pro | Gly | Thr | Val | Leu | Pro | Cys | Pro | Thr | Ser | Val | Pro | Arg | Arg | Pro |
| 121 | GGT | CAA | AGG | AGG | CCA | CCA | CCA | CCA | CCG | CCA | CCG | CCA | CCA | CTA | CCA | CCT | CCG | CCG | CCG | CCG |
| 41 ▸ | Gly | Gln | Arg | Arg | Pro | Pro | Pro | Pro | Pro | Pro | Pro | Leu | Pro | Pro | Pro | Pro | Pro |
| 181 | CCA | CCA | CTG | CCT | CCA | CTA | CCG | CTG | CCA | CCC | CTG | AAG | AAG | AGA | GGG | AAC | CAC | AGC | ACA | GGC |
| 61 ▸ | Pro | Pro | Leu | Pro | Pro | Leu | Pro | Leu | Pro | Pro | Leu | Lys | Lys | Arg | Gly | Asn | His | Ser | Thr | Gly |
| 241 | CTG | TGT | CTC | CTT | GTG | ATG | TTT | TTC | ATG | GTT | CTG | GTT | GCC | TTG | GTA | GGA | TTG | GGC | CTG | GGG |
| 81 ▸ | Leu | Cys | Leu | Leu | Val | Met | Phe | Phe | Met | Val | Leu | Val | Ala | Leu | Val | Gly | Leu | Gly | Leu | Gly |
| 301 | ATG | TTT | CAG | CTC | TTC | CAC | CTA | CAG | AAG | GAG | CTG | GCA | GAA | CTC | CGA | GAG | TCT | ACC | AGC | CAG |
| 101 ▸ | Met | Phe | Gln | Leu | Phe | His | Leu | Gln | Lys | Glu | Leu | Ala | Glu | Leu | Arg | Glu | Ser | Thr | Ser | Gln |
| 361 | ATG | CAC | ACA | GCA | TCA | TCT | TTG | GAG | AAG | CAA | ATA | GGC | CAC | CCC | AGT | CCA | CCC | CCT | GAA | AAA |

TABLE 4-continued

Amino Acid Sequence (SEQ ID NO:2) of FasL,
and FasL Nucleotide Sequence (SEQ ID NO:1)

| | |
|---|---|
| 121▶ | Met His Thr Ala Ser Ser Leu Glu Lys Gln Ile Gly His Pro Ser Pro Pro Glu Lys |
| 421 | AAG GAG CTG AGG AAA GTG GCC CAT TTA ACA GGC AAG TCC AAC TCA AGG TCC ATG CCT CTG |
| 141▶ | Lys Glu Leu Arg Lys Val Ala His Leu Thr Gly Lys Ser Asn Ser Arg Ser Met Pro Leu |
| 481 | GAA TGG GAA GAC ACC TAT GGA ATT GTC CTG CTT TCT GGA GTG AAG TAT AAG AAG GGT GGC |
| 161▶ | Glu Trp Glu Asp Thr Tyr Gly Ile Val Leu Leu Ser Gly Val Lys Tyr Lys Lys Gly Gly |
| 541 | CTT GTG ATC AAT GAA ACT GGG CTG TAC TTT GTA TAT TCC AAA GTA TAC TTC CGG GGT CAA |
| 181▶ | Leu Val Ile Asn Glu Thr Gly Leu Tyr Phe Val Tyr Ser Lys Val Tyr Phe Arg Gly Gln |
| 601 | TCT TGC AAC AAC CTG CCC CTG AGC CAC AAG GTC TAC ATG AGG AAC TCT AAG TAT CCC CAG |
| 201▶ | Ser Cys Asn Asn Leu Pro Leu Ser His Lys Val Tyr Met Arg Asn Ser Lys Tyr Pro Gln |
| 661 | GAT CTG GTG ATG ATG GAG GGG AAG ATG ATG AGC TAC TGC ACT ACT GGG CAG ATG TGG GCC |
| 221▶ | Asp Leu Val Met Met Glu Gly Lys Met Met Ser Tyr Cys Thr Thr Gly Gln Met Trp Ala |
| 721 | CGC AGC AGC TAC CTG GGG GCA GTG TTC AAT CTT ACC AGT GCT GAT CAT TTA TAT GTC AAC |
| 241▶ | Arg Ser Ser Tyr Leu Gly Ala Val Phe Asn Leu Thr Ser Ala Asp His Leu Tyr Val Asn |
| 781 | GTA TCT GAG CTC TCT CTG GTC AAT TTT GAG GAA TCT CAG ACG TTT TTC GGC TTA TAT AAG |
| 261▶ | Val Ser Glu Leu Ser Leu Val Asn Phe Glu Glu Ser Gln Thr Phe Phe Gly Leu Tyr Lys |
| 841 | CTC TAA |
| 281▶ | Leu . . . |

TABLE 5

Amino Acid Sequence of the Mature Heavy Chain (A)
(SEQ ID NO:13) and Light Chain (B)
(SEQ ID NO:14) Variable Regions of
Humanized ABL 364 Antibody (A)

| | |
|---|---|
| 1 | E V Q L L E S G G G L V Q P G G S L R L |
| 21 | S C A A S G F T F S D Y Y M Y W V R Q A |
| 41 | P E K R L E W V A Y I S N G G G S S H Y |
| 61 | V D S V K G R F T I S R D N A K N T L Y |
| 81 | L Q M N S L R A E D T A L Y H C A R G M |
| 101 | D Y G A W F A Y W G Q G T L V T V S S |

(B)

| | |
|---|---|
| 1 | D I V M T Q S P L S L P V T P G E P A S |
| 21 | I S C R S S Q S I V H S N G N T Y L E W |
| 41 | Y L Q K P G Q S P Q L L I S K V S N R F |
| 61 | S G V P D R F S G S G S G T D F T L K I |
| 81 | S R V E A E D V G V Y Y C F Q G S H V P |
| 101 | F T F G Q G T K L E I K |

We claim:

1. A fusion protein comprising a Fas protein recognition moiety of the extracellular domain of a Fas ligand protein and a polypeptide capable of specifically binding to a cell surface marker wherein said fusion protein comprises an amino acid substitution in said Fas ligand protein that decreases the ability of the fusion protein to form dimers, trimers or other aggregates.

2. A fusion protein of claim 1 wherein said substitution occurs at amino acid 148, 189, 192, 244, 168, 170, 229, 232, 248, 234, 241, 242, 245, 246, 247, 249, 272, 279 or 281, as numbered in SEQ ID NO:2.

3. A fusion protein of claim 2 wherein said substitution occurs at the amino acid 232.

4. A fusion protein of claim 3 wherein the amino acid 232 is alanine.

5. A fusion protein of claim 1, wherein the binding polypeptide comprises the heavy (SEQ ID NO:13) and light (SEQ ID NO:14) chain variable regions of a humanized ABL 364 antibody.

6. A fusion protein of claim 1, 2, 3, 4, or 5 further comprising a polypeptide linker between said extracellular domain of the Fas ligand protein and said polypeptide capable of specifically binding the cell surface marker.

7. A fusion protein of claim 1, 2, 3, 4, or 5 that has reduced ability in vitro, relative to soluble FasL protein or FasL protein extracellular domain, to cause death of cells expressing Fas protein.

8. A fusion protein of claim 1, 2, 3, 4, or 5 that has increased ability in vitro to cause death in a first population of cells expressing Fas protein, when such first population of cells are in the presence of a second population of cells to which the polypeptide binds, relative to the absence of such second population of cells.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 846 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..846
        (D) OTHER INFORMATION: /product= "Fas ligand (FasL)"

(xi) SEQUENCE DESCRIPTION: SEQ ID NO:1:

```
ATG CAG CAG CCC TTC AAT TAC CCA TAT CCC CAG ATC TAC TGG GTG GAC      48
Met Gln Gln Pro Phe Asn Tyr Pro Tyr Pro Gln Ile Tyr Trp Val Asp
 1               5                  10                  15

AGC AGT GCC AGC TCT CCC TGG GCC CCT CCA GGC ACA GTT CTT CCC TGT      96
Ser Ser Ala Ser Ser Pro Trp Ala Pro Pro Gly Thr Val Leu Pro Cys
                20                  25                  30

CCA ACC TCT GTG CCC AGA AGG CCT GGT CAA AGG AGG CCA CCA CCA CCA     144
Pro Thr Ser Val Pro Arg Arg Pro Gly Gln Arg Arg Pro Pro Pro Pro
            35                  40                  45

CCG CCA CCG CCA CCA CTA CCA CCT CCG CCG CCG CCA CCA CTG CCT         192
Pro Pro Pro Pro Pro Leu Pro Pro Pro Pro Pro Pro Pro Leu Pro
        50                  55                  60

CCA CTA CCG CTG CCA CCC CTG AAG AAG AGA GGG AAC CAC AGC ACA GGC     240
Pro Leu Pro Leu Pro Pro Leu Lys Lys Arg Gly Asn His Ser Thr Gly
65                  70                  75                  80

CTG TGT CTC CTT GTG ATG TTT TTC ATG GTT CTG GTT GCC TTG GTA GGA     288
Leu Cys Leu Leu Val Met Phe Phe Met Val Leu Val Ala Leu Val Gly
                85                  90                  95

TTG GGC CTG GGG ATG TTT CAG CTC TTC CAC CTA CAG AAG GAG CTG GCA     336
Leu Gly Leu Gly Met Phe Gln Leu Phe His Leu Gln Lys Glu Leu Ala
               100                 105                 110

GAA CTC CGA GAG TCT ACC AGC CAG ATG CAC ACA GCA TCA TCT TTG GAG     384
Glu Leu Arg Glu Ser Thr Ser Gln Met His Thr Ala Ser Ser Leu Glu
           115                 120                 125

AAG CAA ATA GGC CAC CCC AGT CCA CCC CCT GAA AAA AAG GAG CTG AGG     432
Lys Gln Ile Gly His Pro Ser Pro Pro Pro Glu Lys Lys Glu Leu Arg
       130                 135                 140

AAA GTG GCC CAT TTA ACA GGC AAG TCC AAC TCA AGG TCC ATG CCT CTG     480
Lys Val Ala His Leu Thr Gly Lys Ser Asn Ser Arg Ser Met Pro Leu
145                 150                 155                 160

GAA TGG GAA GAC ACC TAT GGA ATT GTC CTG CTT TCT GGA GTG AAG TAT     528
Glu Trp Glu Asp Thr Tyr Gly Ile Val Leu Leu Ser Gly Val Lys Tyr
                165                 170                 175

AAG AAG GGT GGC CTT GTG ATC AAT GAA ACT GGG CTG TAC TTT GTA TAT     576
Lys Lys Gly Gly Leu Val Ile Asn Glu Thr Gly Leu Tyr Phe Val Tyr
            180                 185                 190

TCC AAA GTA TAC TTC CGG GGT CAA TCT TGC AAC AAC CTG CCC CTG AGC     624
Ser Lys Val Tyr Phe Arg Gly Gln Ser Cys Asn Asn Leu Pro Leu Ser
        195                 200                 205
```

```
CAC AAG GTC TAC ATG AGG AAC TCT AAG TAT CCC CAG GAT CTG GTG ATG        672
His Lys Val Tyr Met Arg Asn Ser Lys Tyr Pro Gln Asp Leu Val Met
    210                 215                 220

ATG GAG GGG AAG ATG ATG AGC TAC TGC ACT ACT GGG CAG ATG TGG GCC        720
Met Glu Gly Lys Met Met Ser Tyr Cys Thr Thr Gly Gln Met Trp Ala
225                 230                 235                 240

CGC AGC AGC TAC CTG GGG GCA GTG TTC AAT CTT ACC AGT GCT GAT CAT        768
Arg Ser Ser Tyr Leu Gly Ala Val Phe Asn Leu Thr Ser Ala Asp His
                245                 250                 255

TTA TAT GTC AAC GTA TCT GAG CTC TCT CTG GTC AAT TTT GAG GAA TCT        816
Leu Tyr Val Asn Val Ser Glu Leu Ser Leu Val Asn Phe Glu Glu Ser
        260                 265                 270

CAG ACG TTT TTC GGC TTA TAT AAG CTC TAA                                846
Gln Thr Phe Phe Gly Leu Tyr Lys Leu
    275                 280
```

(2) INFORMATION FOR SEQ ID NO:2:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
                20                  25                  30

Pro Thr Ser Val Pro Arg Arg Pro Gly Gln Arg Arg Pro Pro Pro
            35                  40                  45

Pro Pro Pro Pro Pro Leu Pro Pro Pro Pro Pro Pro Leu Pro
50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
                180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240
```

```
Arg Ser Ser Tyr Leu Gly Ala Val Phe Asn Leu Thr Ser Ala Asp His
            245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
            275                 280
```

(2) INFORMATION FOR SEQ ID NO:3:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

ATGCATGCTC TAGAATGCAG CAGCCCTTCA ATTACCC                                37

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ATGCATGCTC TAGATTAGAG CTTATATAAG CCG                                      33

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ACCACAGGTG TACACCCTGC                                                      20

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATGCATGCGG TACCTTTACT CGGAGACAGG GAGAGG                                36

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATGCATGCGG TACCTGAGTG CCACGGCCGG CAAG                                34

(2) INFORMATION FOR SEQ ID NO:8:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:8:

GGGAAGTATG TACACGGGG                                                 19

(2) INFORMATION FOR SEQ ID NO:9:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:9:

AGCAAATAGG ATCCCCCAGT CC                                             22

(2) INFORMATION FOR SEQ ID NO:10:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:10:

ATGCATGCGG TACCTTAGAG CTTATATAAG CCG                                 33

(2) INFORMATION FOR SEQ ID NO:11:

(i) SEQUENCE CHARACTERISTICS:
              (A) LENGTH: 35 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:11:

ATGCATGCGG TACCCAGCTC TTCCACCTAC AGAAG                               35

(2) INFORMATION FOR SEQ ID NO:12:

(i) SEQUENCE CHARACTERISTICS:
              (A) LENGTH: 31 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:12:

GGACTGGGGG ATCCTATTTG CTTCTCCAAA G                                    31

(2) INFORMATION FOR SEQ ID NO:13:

(i) SEQUENCE CHARACTERISTICS:
        (A) LENGTH: 119 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..119
        (D) OTHER INFORMATION: /note= "mature heavy chain variable
            region of humanized ABL 364 antibody"

(xi) SEQUENCE DESCRIPTION: SEQ ID NO:13:

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Glu Lys Arg Leu Glu Trp Val
        35                  40                  45

Ala Tyr Ile Ser Asn Gly Gly Ser Ser His Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Leu Tyr His Cys
            85                  90                  95

Ala Arg Gly Met Asp Tyr Gly Ala Trp Phe Ala Tyr Trp Gly Gln Gly
            100                 105                 110

Thr Leu Val Thr Val Ser Ser
            115

(2) INFORMATION FOR SEQ ID NO:14:

(i) SEQUENCE CHARACTERISTICS:
        (A) LENGTH: 112 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..112
        (D) OTHER INFORMATION: /note= "mature light chain variable
            region of humanized ABL 364 antibody"

(xi) SEQUENCE DESCRIPTION: SEQ ID NO:14:

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
               100                 105                 110
```

(2) INFORMATION FOR SEQ ID NO:15:

(i) SEQUENCE CHARACTERISTICS:
  (A) LENGTH: 864 base pairs
  (B) TYPE: nucleic acid
  (C) STRANDEDNESS: single
  (D) TOPOLOGY: linear (ii) MOLECULE TYPE: DNA (ix) FEATURE:
  (A) NAME/KEY: CDS
  (B) LOCATION: 1..864
  (D) OTHER INFORMATION: /product= "CH3/FasL domain of Ig-FasL fusion protein"

(xi) SEQUENCE DESCRIPTION: SEQ ID NO:15:

```
CAG CCC CGA GAA CCA CAG GTG TAC ACC CTG CCC CCA TCC CGG GAG GAG         48
Gln Pro Arg Glu Pro Gln Val Tyr Thr Leu Pro Pro Ser Arg Glu Glu
 1               5                  10                  15

ATG ACC AAG AAC CAG GTC AGC CTG ACC TGC CTG GTC AAA GGC TTC TAC         96
Met Thr Lys Asn Gln Val Ser Leu Thr Cys Leu Val Lys Gly Phe Tyr
                20                  25                  30

CCC AGC GAC ATC GCC GTG GAG TGG GAG AGC AAT GGG CAG CCG GAG AAC        144
Pro Ser Asp Ile Ala Val Glu Trp Glu Ser Asn Gly Gln Pro Glu Asn
            35                  40                  45

AAC TAC AAG ACC ACA CCT CCC ATG CTG GAC TCC GAC GGC TCC TTC TTC        192
Asn Tyr Lys Thr Thr Pro Pro Met Leu Asp Ser Asp Gly Ser Phe Phe
50                  55                  60

CTC TAC AGC AAG CTC ACC GTG GAC AAG AGC AGG TGG CAG CAG GGG AAC        240
Leu Tyr Ser Lys Leu Thr Val Asp Lys Ser Arg Trp Gln Gln Gly Asn
65                  70                  75                  80

GTC TTC TCA TGC TCC GTG ATG CAT GAG GCT CTG CAC AAC CAC TAC ACG        288
Val Phe Ser Cys Ser Val Met His Glu Ala Leu His Asn His Tyr Thr
                85                  90                  95

CAG AAG AGC CTC TCC CTG TCT CCG AGT AAA GGT ACC CAG CTC TTC CAC        336
Gln Lys Ser Leu Ser Leu Ser Pro Ser Lys Gly Thr Gln Leu Phe His
               100                 105                 110

CTA CAG AAG GAG CTG GCA GAA CTC CGA GAG TCT ACC AGC CAG ATG CAC        384
Leu Gln Lys Glu Leu Ala Glu Leu Arg Glu Ser Thr Ser Gln Met His
           115                 120                 125

ACA GCA TCA TCT TTG GAG AAG CAA ATA GGA TCC CCC AGT CCA CCC CCT        432
Thr Ala Ser Ser Leu Glu Lys Gln Ile Gly Ser Pro Ser Pro Pro Pro
       130                 135                 140

GAA AAA AAG GAG CTG AGG AAA GTG GCC CAT TTA ACA GGC AAG TCC AAC        480
Glu Lys Lys Glu Leu Arg Lys Val Ala His Leu Thr Gly Lys Ser Asn
145                 150                 155                 160

TCA AGG TCC ATG CCT CTG GAA TGG GAA GAC ACC TAT GGA ATT GTC CTG        528
Ser Arg Ser Met Pro Leu Glu Trp Glu Asp Thr Tyr Gly Ile Val Leu
                165                 170                 175

CTT TCT GGA GTG AAG TAT AAG AAG GGT GGC CTT GTG ATC AAT GAA ACT        576
Leu Ser Gly Val Lys Tyr Lys Lys Gly Gly Leu Val Ile Asn Glu Thr
            180                 185                 190

GGG CTG TAC TTT GTA TAT TCC AAA GTA TAC TTC CGG GGT CAA TCT TGC        624
Gly Leu Tyr Phe Val Tyr Ser Lys Val Tyr Phe Arg Gly Gln Ser Cys
        195                 200                 205
```

```
AAC AAC CTG CCC CTG AGC CAC AAG GTC TAC ATG AGG AAC TCT AAG TAT    672
Asn Asn Leu Pro Leu Ser His Lys Val Tyr Met Arg Asn Ser Lys Tyr
        210                 215                 220

CCC CAG GAT CTG GTG ATG ATG GAG GGG AAG ATG ATG AGC TAC TGC ACT    720
Pro Gln Asp Leu Val Met Met Glu Gly Lys Met Met Ser Tyr Cys Thr
225                 230                 235                 240

ACT GGG CAG ATG TGG GCC CGC AGC AGC TAC CTG GGG GCA GTG TTC AAT    768
Thr Gly Gln Met Trp Ala Arg Ser Ser Tyr Leu Gly Ala Val Phe Asn
                245                 250                 255

CTT ACC AGT GCT GAT CAT TTA TAT GTC AAC GTA TCT GAG CTC TCT CTG    816
Leu Thr Ser Ala Asp His Leu Tyr Val Asn Val Ser Glu Leu Ser Leu
        260                 265                 270

GTC AAT TTT GAG GAA TCT CAG ACG TTT TTC GGC TTA TAT AAG CTC        861
Val Asn Phe Glu Glu Ser Gln Thr Phe Phe Gly Leu Tyr Lys Leu
        275                 280                 285

TAA                                                                 864

(2) INFORMATION FOR SEQ ID NO:16:

(i) SEQUENCE CHARACTERISTICS:
        (A) LENGTH: 287 amino acids
        (B) TYPE: amino acid
        (D) TOPOLOGY: linear (ii) MOLECULE TYPE: protein (xi) SEQUENCE DESCRIPTION: SEQ ID NO:16:

Gln Pro Arg Glu Pro Gln Val Tyr Thr Leu Pro Pro Ser Arg Glu Glu
1               5                   10                  15

Met Thr Lys Asn Gln Val Ser Leu Thr Cys Leu Val Lys Gly Phe Tyr
            20                  25                  30

Pro Ser Asp Ile Ala Val Glu Trp Glu Ser Asn Gly Gln Pro Glu Asn
        35                  40                  45

Asn Tyr Lys Thr Thr Pro Pro Met Leu Asp Ser Asp Gly Ser Phe Phe
    50                  55                  60

Leu Tyr Ser Lys Leu Thr Val Asp Lys Ser Arg Trp Gln Gln Gly Asn
65                  70                  75                  80

Val Phe Ser Cys Ser Val Met His Glu Ala Leu His Asn His Tyr Thr
                85                  90                  95

Gln Lys Ser Leu Ser Leu Ser Pro Ser Lys Gly Thr Gln Leu Phe His
            100                 105                 110

Leu Gln Lys Glu Leu Ala Glu Leu Arg Glu Ser Thr Ser Gln Met His
        115                 120                 125

Thr Ala Ser Ser Leu Glu Lys Gln Ile Gly Ser Pro Ser Pro Pro
130                 135                 140

Glu Lys Lys Glu Leu Arg Lys Val Ala His Leu Thr Gly Lys Ser Asn
145                 150                 155                 160

Ser Arg Ser Met Pro Leu Glu Trp Glu Asp Thr Tyr Gly Ile Val Leu
                165                 170                 175

Leu Ser Gly Val Lys Tyr Lys Gly Gly Leu Val Ile Asn Glu Thr
            180                 185                 190

Gly Leu Tyr Phe Val Tyr Ser Lys Val Tyr Phe Arg Gly Gln Ser Cys
        195                 200                 205

Asn Asn Leu Pro Leu Ser His Lys Val Tyr Met Arg Asn Ser Lys Tyr
    210                 215                 220

Pro Gln Asp Leu Val Met Met Glu Gly Lys Met Met Ser Tyr Cys Thr
225                 230                 235                 240
```

```
Thr Gly Gln Met Trp Ala Arg Ser Ser Tyr Leu Gly Ala Val Phe Asn
                245                 250                 255

Leu Thr Ser Ala Asp His Leu Tyr Val Asn Val Ser Glu Leu Ser Leu
                260                 265                 270

Val Asn Phe Glu Glu Ser Gln Thr Phe Phe Gly Leu Tyr Lys Leu
                275                 280                 285

(2) INFORMATION FOR SEQ ID NO:17:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Peptide
        (B) LOCATION: 6..40
        (D) OTHER INFORMATION: /note= "amino acid residues 6-40 may be
            present or absent"

(xi) SEQUENCE DESCRIPTION: SEQ ID NO:17:

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser
            35                  40
```